United States Patent [19]

Tung

[11] Patent Number: 5,773,671
[45] Date of Patent: Jun. 30, 1998

[54] PROCESS FOR PURIFYING 1,1-DICHLORO-2,2,2-TRIFLUOROETHANE AND 1-CHLORO-1,2,2,2-TETRAFLUOROETHANE

[75] Inventor: Hsueh Sung Tung, Getzville, N.Y.

[73] Assignee: Allied Signal, Morristown, N.J.

[21] Appl. No.: 768,338

[22] Filed: Dec. 17, 1996

Related U.S. Application Data

[63] Continuation of Ser. No. 144,264, Oct. 28, 1993, abandoned.

[51] Int. Cl.[6] .................................................. C07C 17/38
[52] U.S. Cl. ............................................................ 570/177
[58] Field of Search ................................. 570/168, 169, 570/177

[56] References Cited

U.S. PATENT DOCUMENTS

| | | |
|---|---|---|
| 3,258,500 | 6/1966 | Swamer et al. . |
| 3,755,477 | 8/1973 | Firth et al. . |
| 4,766,260 | 8/1988 | Manzer et al. ...................... 570/168 |
| 4,843,181 | 6/1989 | Gumprecht et al. . |
| 4,944,846 | 7/1990 | Manzer et al. . |
| 5,091,601 | 2/1992 | Carmello et al. . |

FOREIGN PATENT DOCUMENTS

| | | |
|---|---|---|
| 0 298 662 | 1/1989 | European Pat. Off. . |
| 0 313 061 | 4/1989 | European Pat. Off. . |
| 0 450 467 A3 | 9/1991 | European Pat. Off. . |
| 0 537 760 A3 | 4/1993 | European Pat. Off. . |
| 6385175 | 10/1989 | Japan . |
| 111733 | 4/1990 | Japan . |

*Primary Examiner*—Alan Siegel
*Attorney, Agent, or Firm*—Jay P. Friedenson; Collen D. Szuch

[57] ABSTRACT

The invention relates to a novel process for purifying HCFC-123 and HCFC-124 comprising:
(a) reacting a fluorination reaction product comprising HCFC-123 and HCFC-123a and/or HCFC-124 and HCFC-124a wherein at least one of said HCFC-123a or HCFC-124a is present in an amount not less than 5 weight percent relative to HCFC-123 or HCFC-124 respectively in the product with anhydrous HF in the presence of a fluorination catalyst under conditions such that the amount of HCFC-123a and/or HCFC-124a relative to HCFC-123 and/or HCFC-124 respectively in the product is reduced to less than 5 weight percent.

The pure product (i.e., HCFC-123 or HCFC-124) may be used in a variety of applications including solvent, refrigerant, sterilant gas and blowing agent applications.

26 Claims, No Drawings

PROCESS FOR PURIFYING 1,1-DICHLORO-2,2,2-TRIFLUOROETHANE AND 1-CHLORO-1,2,2,2-TETRAFLUOROETHANE

This application is a continuation of application Ser. No. 08/144,264 filed Oct. 28, 1993 now abandoned.

The invention relates to a novel method of purifying 1,1-dichloro-2,2,2-trifluoroethane (HCFC-123) and 1-chloro-1,2,2,2-tetrafluoroethane (HCFC-124). Specifically, the invention relates to a method of removing the 1,2-dichloro-1,2,2-trifluoroethane (HCFC-123a) isomer from 1,1-dichloro-2,2,2-trifluoroethane and the 1-chloro-1,1,2,2-tetrafluoroethane (HCFC-124a) isomer from 1-chloro-1,2,2,2-tetrafluoroethane. The pure product (i.e. either HCFC-123 or HCFC-124) may be used in a variety of applications including solvent, refrigerant, sterilant gas and blowing agent applications.

Traditionally, chlorofluorocarbons (CFCs) like trichlorofluoromethane (CFC-11), dichlorodifluoromethane (CFC-12) and 1,1,2-trichloro-1,2,2-trifluoroethane (CFC-113) have been used as refrigerants, blowing agents and diluents for gaseous sterilization. These materials, however, are suspect since they are believed to contribute to the stratospheric ozone depletion problem. The fluorocarbon industry has therefore focused its attention on developing stratospherically safer alternatives to these materials. HCFC-123 and HCFC-124 are candidate replacement materials. These materials have much lower ozone depletion potentials than their CFC predecessors and offer substantially the same performance advantages. As a result, several manufacturers have announced plans to construct plants to commercialize these materials.

PAFT II (Panel for Advancement of Fluorocarbon Test) which defines HCFC-123 and HCFC-124 product purity has set specifications for HCFC-123a and HCFC-124a isomer concentrations at 5% each. Because the physical properties of HCFC-123a and HCFC-124a are very similar to their counterparts (i.e., HCFC-123 and HCFC-124 respectively), they cannot be separated using conventional separation processes, such as distillation. Because of this, the art has looked to isomerization as a means of removing these isomers. Japanese Application No.: Sho 63-85175, published Oct. 16, 1989 discloses a liquid phase process for the catalyzed isomerization of HCFC-123a. This process suffers several drawbacks. It requires long reaction times and generates many undesirable by-products. Kokai Patent Publication No: 111733, published Apr. 24, 1990 discloses the catalyzed vapor phase isomerization of HCFC-123a. This process also results in the production of many undesirable by-products. In addition, these processes like all isomerization reactions require an acid free feed stock. This means that prior to isomerization, acids such as HF and HCl must be removed making these processes less economical. Thus, a need exists for a method of removing HCFC-123a and HCFC-124a from their counterparts which overcomes the above described disadvantages and results in improved HCFC-123 and HCFC-124 product quality and meeting PAFT specifications.

DESCRIPTION OF THE INVENTION

We have discovered that the fluorination of HCFC-123a and HCFC-124a proceeds preferentially over the fluorination of HCFC-123 and HCFC-124. See, Examples 1–11 below. These reactivity differences may be used to purify crude HCFC-123 and HCFC-124 by removing HCFC-123a and HCFC-124a respectively and thus reducing the levels of these isomers in accordance with the purity standards set by PAFT II.

The invention relates to a novel process for purifying HCFC-123 and HCFC-124 comprising:

(a) reacting a fluorination reaction product comprising HCFC-123 and HCFC-123a and/or HCFC-124 and HCFC-124a wherein at least one of said HCFC-123a or HCFC-124a is present in an amount not less than 5 weight percent relative to HCFC-123 or HCFC-124 respectively in the product with anhydrous HF in the presence of a fluorination catalyst under conditions such that the amount of HCFC-123a and/or HCFC-124a relative to HCFC-123 and/or HCFC-124 respectively in the product is reduced to less than 5 weight percent.

For purposes of this invention, the term "fluorination reaction product" shall mean the product produced when an organic reactant and fluorinating agent (such as HF) are brought together under conditions (optionally including catalyst) such that at least one reactant is fluorinated.

HCFC-123, HCFC-123a, HCFC-124 and HCFC-124a are all commercially available materials. These compounds may be purchased, for example, from AlliedSignal Inc. of Morristown, N.J. Alternatively, HCFC-123 and HCFC-123a may be produced in accordance with the processes set forth in U.S. Pat. No. 3,755,477 or U.S. Pat. No. 3,258,500 and HCFC-124 and HCFC-124a may be prepared in accordance with the processes set forth in U.S. Pat. Nos. 3,755,477 and 4,843,181.

Any suitable fluorination catalyst as is well known in the art may be employed in the present invention. Suitable fluorination catalysts include but are not limited to chrome oxide, modified chrome oxide and alumina-supported transition metal halide catalysts. The modified chrome oxide catalysts include $Cr_2O_3$ supported on carbon or alumina or aluminum fluoride, and a mixture of chrome oxide alumina. Transition metal halides can be impregnated on an alumina support to produce a selective fluorination catalyst. These transition metal halides include cobalt, nickel, manganese, rhodium and ruthenium halide. These transition metal halides can also be impregnated onto a support of chrome oxide and alumina to improve their selectivity.

The temperature at which the organics, hydrogen fluoride and fluorination catalyst are reacted can vary, for example, from about 250° to about 450° C., preferably, from about 300° to about 400° C. and most preferably from about 310° to about 375° C. with a contact time of, for example, about 1 to about 120 seconds, preferably from about 5 to about 90 seconds and most preferably from about 10 to about 60 seconds. For purposes of this invention, contact time shall mean the time required for the gaseous reactants to pass through the catalyst bed assuming that the catalyst bed is 100% void.

The molar ratio of HF to organics can range, for example, from about 12:1–1:1, preferably from about 10:1–2:1 and most preferably from about 8:1–3:1.

Pressure is not critical. Atmospheric and super atmospheric pressure are the most convenient and are therefore preferred. In particular, high reaction pressure is desirable because it makes separation of the HF from HCl easier.

The reaction is preferably conducted in an apparatus made of corrosion resistant material such as Inconel or Monel.

The HCFC-123, HCFC-123a, HCFC-124, HCFC-124a, hydrogen fluoride and fluorination catalyst components of the invention are known materials. Preferably, they should be used in high purity so as to avoid the introduction of adverse influences upon the reaction system. The hydrogen fluoride used in the invention is preferably anhydrous (i.e. containing less than about 0.02 weight percent $H_2O$).

The invention is more fully illustrated by the following non-limiting examples.

EXAMPLE 1

(a) Catalyst Preparation—aluminum/chromium oxide co-extrudate. Ground chromium oxide powder with a median particle size of about 37 microns was mixed with aluminum oxide hydroxide powder with a median particle size of less than about 0.2 microns. The mole ratio of aluminum:chromium was about 70:30. Six (6) weight percent nitric acid was added to the mixed oxides and the mixture was kneaded to form a thick paste. The paste was then charged to a Brabender and extruded using a 1/16 inch single hole die. The extrudate was dried in an oven overnight at 82°–90° C. and was then calcined in a muffle furnace at about 490° C. for 2–3 hours. After cooling, the extrudate was sized to an approximate L/D (length/diameter) of 3. The surface area of the extrudate was 229 $m^2/g$.

(b) Impregnation with metal salt. 245 g of aluminum/chromium oxide extrudate prepared in step 1(a) were placed in about 260 ml of 0.24M $CoCl_2$ solution for approximately 16–20 hours. The wet extrudate was filtered and dried in a vacuum oven at about 100°–110° C. for 2.5 days. The $CoCl_2$ loading was 1.4 wt. %.

(c) Calcination and HF Pretreatment. About 100–110 ml catalyst was charged into a ½ inch Monel reactor and a steady stream of air flowed through the catalyst bed (about 2–3 l/min). The temperature of the reactor was then raised rapidly to 400° C. and held for 16 hours. Subsequently, the temperature was lowered to 200° C. and air was replaced with nitrogen at a feed rate of about 0.5–1.5 l/min. HF was then pumped in the reactor at a rate of 1–2 ml/min. After the exotherm disappeared, the nitrogen was turned off and the temperature raised to 400° C. and held for 8 hours. The catalyst was then ready for use.

EXAMPLES 2–3

Approximately 110 ml of the catalyst prepared in Example 1(a)–(c) was charged to a ½ inch Monel reactor. The organic feed (see Table I below) and anhydrous HF were then fed simultaneously to the reactor and reacted under the conditions set forth in Table I below. The resulting product was analyzed using an on-line Perkin Elmer 8500 gas chromatograph and the results are reported in Table I.

TABLE I

| Example | 2 | 3 |
|---|---|---|
| Catalyst: | $CoCl_2/Al_2O_3/Cr_2O_3$ | |
| Feed: | 90 wt % HCFC-123/10 wt % HCFC-123a | |
| HF/Org. Mole Ratio: | ← 3.7 → | |
| Pressure (psig) | ← 200 → | |
| Temp. (°C.): | 340 | 350 |
| Contact Time (sec): | 21 | 21 |
| Conversion (%): | | |
| HCFC-123/a: | 28 | 43 |
| Selectivity (%): | | |
| HFC-125 | 5.0 | 8.7 |
| HCFC-124a | 2.5 | 1.8 |
| HCFC-124 | 89.6 | 87.0 |
| Combined 120's | 97.0 | 97.5 |
| Isomer Concentration (%): | | |
| 124a in 124/124a mix | 2.7 | 2.0 |
| 123a in 123/123a mix | 4.1 | 1.9 |

The results show that the HCFC-123a concentration in the product relative to HCFC-123 was reduced to less than 5 wt %. Although HCFC-124a was formed as a by product, the concentration of this isomer was also less than 5 wt % relative to HCFC-124 in the product. The process is also a selective one, producing 97% of commercially desirable materials.[1]

[1] HFC-125 or pentafluoroethane has commercial application as refrigerant and a diluent in sterilant gas compositions.

These Examples also demonstrate that a higher reaction temperature results in increased HCFC-123a conversion and decreased HCFC-124a production. In other words, higher temperature is preferred to remove the HCFC-123a and HCFC-124a isomers from their counterparts.

EXAMPLES 4–5

Using the catalyst prepared in Example 1(a)–(c) above, the experiment described in Examples 2–3 above was repeated using the feed and conditions described in Table II below. The resulting product was analyzed using an on-line Perkin Elmer 8500 gas chromatograph and the results are reported in Table II.

TABLE II

| Example | 4 | 5 |
|---|---|---|
| Catalyst: | $CoCl_2/Al_2O_3/Cr_2O_3$ | |
| Feed: | 81 wt % HCFC-123/19 wt % HCFC-123a | |
| HF/Org. Mole Ratio: | 4.4 | 1.9 |
| Pressure (psig) | ← 200 → | |
| Temp. (°C.): | ← 350 → | |
| Contact Time (sec): | 30 | 30 |
| Conversion (%): | | |
| HCFC-123/a: | 64 | 48 |
| Selectivity (%): | | |
| HFC-125 | 19.4 | 13.9 |
| HCFC-124a | 1.3 | 1.9 |
| HCFC-124 | 78.1 | 81.6 |
| Combined 120's | 98.8 | 97.3 |
| Isomer Concentration (%): | | |
| 124a in 124/124a mix | 1.6 | 2.3 |
| 123a in 123/123a mix | 0.8 | 0.7 |

[1] HFC-125 or pentafluoroethane has commercial application as a refrigerant and a diluent in sterilant gas compositions.

The results of Examples 4 and 5 show that the HCFC-123a concentration in the product relative to HCFC-123 was reduced to less than 5 wt % and, although HCFC-124a was formed as a by product, the concentration of this isomer was also less than 5 wt % relative to HCFC-124 in the product.

We believe that these Examples also demonstrate that a higher HF:organics mole ratio results in a greater HCFC-123a conversion and a lower HCFC-124a concentration.

EXAMPLES 6–7

Using the catalyst prepared in Example 1(a)–(c) above, the experiment described in Examples 2–3 above is repeated under the conditions described in Table I above using a 90 wt % HCFC-124/10 wt % HCFC-124a feed. The resulting product is analyzed using an on-line Perkin Elmer 8500 gas chromatograph. The results indicate that the HCFC-124a concentration relative to HCFC-124 in the product is reduced to less than 5 wt %.

EXAMPLES 8–9

Using the catalyst prepared in Example 1(a)–(c) above, the experiment described in Examples 4–5 above is repeated under the conditions described in Table II above using an 81 wt % HCFC-124/19 wt % HCFC-124a feed. The resulting product is analyzed using an on-line Perkin Elmer 8500 gas chromatograph. The results indicate that the HCFC-124a concentration relative to HCFC-124 in the product is reduced to less than 5 wt %.

EXAMPLES 10–11

Into a ½ inch Monel reactor is placed 110 ml of the catalyst of Example 1(a)–(c) and the temperature of the reactor raised to 310° C. and the pressure 200 psig. Then, perchloroethylene and HF are simultaneously added to the reactor at an HF:organics mole ratio of 8:1. The contact time is 36 seconds. The product is analyzed using an on-line Perkin Elmer 8500 gas chromatograph and is found to primarily contain the indicated compounds in the approximate wt % shown:

| wt % | compound |
|---|---|
| 23 | HCFC-123 |
| 5 | HCFC-123a |
| 3 | HCFC-124 |
| 0.5 | HCFC-124a |
| 0.5 | HCFC-125 |
| 43 | Perchloroethylene |
| 25 | Other recyclable products |

This reaction product and HF are then charged simultaneously to a ½ inch Monel reactor containing the catalyst of Example 1(a)–(c). The temperature and pressure of the reactor are maintained at 340° C. and 200 psig respectively. The HF:organics mole ratio is 5:1 and the contact time is 30 seconds. The product is analyzed using an on-line Perkin Elmer 8500 gas chromatograph and found to contain less than 5 wt % HCFC-123a and HCFC-124a relative to HCFC-123 and HCFC-124 respectively in the product.

The above Examples point up perhaps the biggest advantage of the process of the invention over the prior art. The process of the invention allows one to remove the undesirable isomers (HCFC-123a and HCFC-124a) on line without any prior purification (i.e., scrubbing to remove acid and distillation to remove recyclables (if not removed, these will result in the production of even more undesirable by-products).

I claim:

1. A process for purifying HFCF-123 and HCFC-124 comprising:
    reacting a fluorination reaction product comprising HCFC-123 and HCFC-123a and/or HCFC-124 and HCFC-124a wherein at least one of said HCFC-123a or HCFC-124a is present in an amount of not less than 5 weight percent relative to HCFC-123 or HCFC-124 respectively in the product with anhydrous HF in the presence of a fluorination catalyst under conditions such that the amount of HCFC-123a and/or HCFC-124a relative to HCFC-123 and/or HCFC-124 respectively in the product is reduced to less than 5 weight percent wherein the reaction product and HF are reacted in an HF:reaction product mole ratio of from about 12:1–1:1.

2. The process of claim 1 wherein said catalyst is selected from the group consisting of chrome oxide, modified chrome oxide and alumina-supported transition metal halides.

3. The process of claim 2 wherein said catalyst is chrome oxide.

4. The process of claim 1 wherein said reaction is conducted at a temperature of from about 250° to about 450° C.

5. The process of claim 3 wherein said reaction is conducted at a temperature of from about 310° to about 375° C.

6. The process of claim 1 wherein said reaction is conducted at super atmospheric pressure.

7. The process of claim 5 wherein said reaction is conducted at super atmospheric pressure.

8. The process of claim 7 wherein said fluorination reaction product and hydrogen fluoride are reacted in and HF:fluorination reaction product mole ratio of from about 8:1–3:1.

9. The process of claim 1 wherein said reaction product and HF are reacted in the presence of said catalyst for a contact time of from about 1 to about 120 seconds.

10. The process of claim 8 wherein said reaction product and HF are reacted in the presence of said catalyst for a contact time of from about 10 to about 60 seconds.

11. The process of claim 3 wherein said catalyst is prepared by blending aluminum oxide hydroxide and chromium oxide together in the presence of a solvent and extruding the blend.

12. The process of claim 11 wherein said catalyst is impregnated with a metal salt.

13. The process of claim 12 wherein said catalyst is calcined after extrusion.

14. The process of claim 13 wherein said catalyst is pretreated with hydrogen fluoride after calcination.

15. The process of claim 1 wherein the reaction product comprises HCFC-124 and HCFC-124a.

16. The process of claim 1 wherein the reaction product consists essentially of HCFC-124 and HCFC-124a.

17. The process of claim 1 wherein the reaction product comprises each of HCFC-123, HCFC-123a, HCFC-124 and HCFC-124a.

18. The process of claim 1 wherein the fluorination reaction product consists essentially of HCFC-123 and HCFC-123a.

19. A process comprising the step of:
    reacting a fluorination reaction product consisting essentially of HCFC-123 and HCFC-123a, wherein the HCFC-123a is present in an amount not less than 5 weight percent relative to HCFC-123, with anhydrous HF in the presence of a fluorination catalyst, wherein the fluorination reaction product and HF are reacted in a HF:fluorination reaction product mole ratio of from about 8:1–3:1 and a temperature of from about 310° to about 375° C. for a contact time of from about 1 to about 120 seconds so that the amount of HCFC-123a relative to HCFC-123 in the fluorination reaction product is reduced to less than 5 weight percent.

20. The process of claim 19 wherein the fluorination catalyst is selected from the group consisting of chrome oxide, modified chrome oxide and alumina-supported transition metal halides.

21. The process of claim 19 wherein the fluorination catalyst is chrome oxide.

22. A process for purifying HCFC-123 comprising the step of:
    reacting a fluorination reaction product comprising HCFC-123 and HCFC-123a, wherein the HCFC-123a is present in an amount not less than 5 weight percent relative to HCFC-123, with anhydrous HF so that the amount of HCFC-123a relative to HCFC-123 in the fluorination reaction product is reduced to less than 5 weight percent, wherein the reaction is carried out in the presence of a fluorination catalyst selected from the group consisting of chrome oxide catalyst and modified chrome oxide catalyst and wherein the fluorination reaction product and HF are reacted in a HF:fluorination reaction product mole ratio of from about 12:1 to about 1:1 and a temperature of from about 250° to about 450° C.

23. The process of claim 22 wherein the fluorination catalyst is a modified chrome oxide catalyst selected from the group consisting of chrome oxide catalyst supported on alumina or carbon and mixtures of chrome oxide and alumina.

24. The process of claim 23 wherein the modified chrome oxide catalyst is a mixture of chrome oxide and alumina.

25. The process of claim 23 wherein the modified chrome oxide catalyst is chrome oxide catalyst supported on alumina.

26. The process of claim 22 wherein the fluorination catalyst is chrome oxide catalyst.

\* \* \* \* \*